United States Patent
Inoue et al.

[11] Patent Number: 6,066,118
[45] Date of Patent: May 23, 2000

[54] MEDICAL DEVICE AND PRODUCTION THEREOF

[75] Inventors: Hiroyuki Inoue, Kusatsu; Takeshi Nizuka, Ohtsu, both of Japan

[73] Assignee: Nissho Corporation, Osaka-Fu, Japan

[21] Appl. No.: 09/203,364

[22] Filed: Dec. 2, 1998

Related U.S. Application Data

[62] Division of application No. 08/907,506, Aug. 8, 1997, Pat. No. 5,891,109.

[30] Foreign Application Priority Data

Aug. 9, 1996 [JP] Japan .................................. 8-210726

[51] Int. Cl.⁷ ........................................................ A61M 5/32
[52] U.S. Cl. ........................... 604/265; 428/423.1; 427/336
[58] Field of Search ..................... 604/265, 266, 604/267, 523, 525; 428/423, 424.4, 425.5, 447, 448, 482, 483; 427/2.28, 2.25, 2.9, 336

[56] References Cited

U.S. PATENT DOCUMENTS

| | | |
|---|---|---|
| 4,943,460 | 7/1990 | Markle et al. ................. 604/265 X |
| 5,001,009 | 3/1991 | Whitbourne . |
| 5,229,211 | 7/1993 | Murayama et al. ............... 604/523 X |
| 5,576,072 | 11/1996 | Hosteller et al. . |
| 5,662,960 | 9/1997 | Hosteller et al. . |

FOREIGN PATENT DOCUMENTS

| | | |
|---|---|---|
| 133181 | 7/1989 | Japan . |
| 3-236854 | 10/1991 | Japan . |
| 412145 | 3/1992 | Japan . |
| 67426 | 1/1994 | Japan . |

*Primary Examiner*—Wynn Wood Coggins
*Assistant Examiner*—A. T. Nguyen
*Attorney, Agent, or Firm*—Birch, Stewart, Kolasch & Birch, LLP

[57] ABSTRACT

A medical device having good surface lubricity in the wet condition, high frictional durability and surface lubricity stability includes a body and a smoothing or lublicating coating on a surface of the body. The coating is produced by applying a solution of a mixture of maleic anhydride high polymer and polyurethane having allophanate bond on a surface of the body, insolubilizing the resultant coating by heating, and then hydrophilizing the coating with a hydrophilizing agent such as ammonia, amine or alcohol.

2 Claims, 3 Drawing Sheets

MEDICAL DEVICE AND PRODUCTION THEREOF

This application is a divisional of copending Application No. 08/907,506, filed Aug. 8, 1997, now U.S. Pat. No. 5,891,109, the entire contents of which are hereby incorporated by reference.

FIELD OF THE INVENTION

The present invention relates to a medical device such as, for example, catheters and guide wires or stylets for guiding a catheter to an objective site of human tissue or coelom such as, for example, blood vessel, digestive tract, urether, tracheae, bile duct and the like.

DESCRIPTION OF THE PRIOR ART

Medical devices such as, for example, catheters put into the human tissue or coelom such as blood vessel, digestive tract, ureter, tracheae, bile duct and the like, guide wires or stylets used for guiding a catheter to an objective site of the tissue. Such medical devices have to be put into the objective site of the tissue correctly without injuring the tissue. Also, the medical devices are required to have a good lubricity so as not to injure the mucous by friction or to cause inflammation during insertion in the tissue.

For these reasons, it is the general practice to use a low friction material such as fluoroplastics, polyethylene and the like as a material for medical device. Further, in order to improve the slipping property of the medical device as well as to prevent the blood from clotting, the medical device has been provided on the surface thereof with a coating of fluoroplastics, silicone resin, or urethane resin, or coated with silicone oil, olive oil, glycerine, Xylocaine (Tradename) jelly or the like. However, these processes have little effect and there is such a defect that the frictional resistance can not be lowered sufficiently.

These problems have been overcome by a medical device proposed in Japanese patent unexamined publication No. 6-7426. The medical device is provided with a lublicating film of methyl vinyl ether-maleic anhydride copolymer and is produced by immersing a base member of polyurethane in a solution of methyl vinyl ether-maleic anhydride copolymer dissolved in methyl ethyl ketone, drying the base member and treating it with water to form a lublicating film on the surface of the base member. Such a medical device shows good surface lubricity in the wet condition, but never keeps the lubricity up. For example, guide wires with such a lubricating film has a tendency to lose the surface lubricity step by step when subjected to repeated stress in the catheter.

Also, in Japanese patent examined publication No. 1-33181, there has been proposed a medical device having a thin film of a maleic anhydride high polymer covalently bonded to a reactive functional group present on surfaces of a body thereof. This device shows good surface lubricity in the wet condition and possesses high durability of lubricity. However, the body has to be treated with a solution of an organic compound having a functional group such as, for example, isocyanate group, amino group, aldehide group or epoxy group to provide the functional group on the surfaces of the body. Thus, there is a fear of unreacted compounds remaining on the surface of the medical device, causing a problem with reguard to the safety of a patient.

Further, in Japanese patent examined publication No. 4-12145, there has been proposed a medical device covered with a water-soluble polymer or a derivative thereof which are ionically bonded to a functional group present on surfaces of a base member. Although this device shows good surface lubricity in the wet condition, the polymer film is peeled off in a solution containing ions such as physiological saline since molecules of the polymer are fixed on the surface of the device body by ionic bonding.

In Japanese patent unexamined publication No. 3-2366854, there has been proposed a medical device provided on a surface thereof with a coating of a half ester of methyl vinyl ether-maleic anhydride copolymer or a derivative thereof partially cross-linked by diisocyanate. This device shows good surface lubricity in the wet condition and possesses high durability of lubricity. However, there is a fear of an unreacted compound with the diisocianate group remaining on the surface of the medical device since the compound with the diisocianate group has to be mixed with the reaction system for formation of the coating. This residual unreacted compound causes a problem with reguard to the safety of a patient. Further, the half ester of methyl vinyl ether-maleic anhydride copolymer is poor in surface lubricity as the copolymer by itself has a hydrophobic group. In addition, the coating thereof and the surface lubricity is lowered because of the molecular chains of the copolymer being restrained by a cross-linked structure. The above coating is formed by directly coating a solution of methyl vinyl ether-maleic anhydride copolymer or a derivative thereof on the surface of the device body, but a pot life of the solution is very short and of the order of only 2 hours.

SUMMARY OF THE INVENTION

It is therefore an object of the present invention to provide a medical device which shows good surface lubricity in the wet condition, possesses high frictional durability, and keeps the surface lubricity stably.

Another object of the present invention is to provide a method for producing a medical device which shows good surface lubricity in the wet condition, possesses high frictional durability, and keeps the surface lubricity stably.

The above and other objects of the present invention are solved by providing a medical device comprising a body and a smoothing or lublicating coating provided on a surface thereof, said coating being composed of a mixture of maleic anhydride high polymer and polyurethane having allophanate bond, said coating being insolubilized by heating and hydrophilized with a hydrophilizing agent.

According to the present invention, there is also provided a method for producing medical devices comprising the steps of applying a solution of a mixture of maleic anhydride high polymer and polyurethane having allophanate bond on a surface of a body, insolubilizing the resultant coating by heating, and then hydrophilizing the coating with a hydrophilizing agent. The hydrophilizing agent is preferably selected from the group consisting of ammonia, amines and alcohols.

In a preferred embodiment, the coating can be formed on a surface of a body of a synthetic resin by dipping the body in a mixed solution of maleic anhydride high polymer and polyurethane with the allophanate bond. The resultant coating is insolubilized by subjecting the resultant coating to a suitable thermal treatment as the maleic anhydride high polymer reacts with the polyurethane. The resultant insolubilized coating is hydrophilized with a hydrophilizing agent such as ammonia, amine or alcohol. This hydrophilized coating shows a good surface lubricity in the wet condition. Since the maleic anhydride high polymer has been insolubilized by the reaction with polyurethane, the coating becomes insoluble and hard to peel off by repeated friction, thus making it possible to maintain the surface lubricity persistently.

As a body, there may be used those made of synthetic resins such as polyurethane, polyamide, polyvinyl chloride, polyester and the like, or metal wires coated with these synthetic resins. The maleic anhydride high polymer, which is one of the components constituting the coating, has a function to develop the surface lubricity in the wet condition by hydrophilization. The maleic anhydride high polymer includes methyl vinyl ether-maleic anhydride copolymer, ethylene-maleic anhydride copolymer, 1-octadecene-maleic anhydride copolymer, stylene-maleic anhydride copolymer and the like.

The hydrophilizing agent reacts with the maleic anhydride high polymer to give the hydrophilicity to the coating. Preferred hydrophilizing agents include ammonia; amines such as methyl amine, ethyl amine, propyl amine, etc,; and alcohols such methyl alcohol, ethyl alcohol, propyl alcohol, butyl alcohol, etc.

If the maleic anhydride high polymer is coated simply on the medical device body, for example, a bare guide wire, the produced guide wire develops no surface lubricity even in the wet condition. However, this problem is solved by hydrophilization of the guide wire with the hydrophilizing agent. The hydrophilized guide wire can develop the surface lubricity sufficient for the practical use in the wet condition, but there arises a new problem that, when such a guide wire is inserted in a catheter and then introduced into the blood vessel, the maleic anhydride high polymer may be eluted from the coating on the guide wire with the blood or that the coating may be peeled off from the guide wire, resulting in a decrease of the surface lubricity of the guide wire. Thus, it is required to make the coating of the maleic anhydride high polymer insoluble before hydrophilizing the same.

According to the present invention, this new problem is solved by mixing the maleic anhydride high polymer with polyurethane and heating the resultant mixture after coating. Preferred polyurethane are those soluble in a solvent for the maleic anhydride high polymer and having allophanate bond. The maleic anhydride high polymer is insolubilized by mixing it with the above polyurethane and heating the resultant mixture. The reaction mechanism is not specified clearly but this can be presumed as follows: The allophanate bond reversively decomposes to isocyanate group on heating, and the resulting isocyanate group reacts with vapor in the atmosphere to produce an amino group. This amino group reacts with the carboxyl group of the maleic anhydride high polymer to produce amide bond. The reaction proceeds three dimensionally to produce an insoluble coating. The solution of the mixture of the maleic anhydride high polymer and polyurethane has a pot life of about one day, which is much longer than that of the solution of the prior art employing diisocyanate with the pot life of about 2 hours.

The above presumption is supported by the fact that isocyanate is produced from polyurethane by heating. The formation of isocyanate due to heating of polyurethane can be confirmed by taking infrared absorption spectrum of polyurethane singly before and after heat treatment thereof. FIGS. 1 and 2 shows infrared absorption spectra of ether-ester type polyurethane (Sanplane 1B -802 of SANYO CHEMICAL INDUSTRIES, Ltd., weight-average molecular weight: 50,000) before and after heat treatment thereof. From these figures, it can been seen that the spectrum indicates a peak resulting from the formation of isocyanate around 2260 $m^{-1}$.

As mentioned above, the coating of the mixture of the maleic anhydride high polymer and polyurethane may be formed on the body by dipping the body in a solution of the mixture, removing the solvent in the wet coating on the body, and then heating the coating. As a solvent for the mixture, there may be used organic solvents such as, for example, acetone, methyl ethyl ketone, dimethyl formamide, dimethyl acetamide, tetrahydrofuran and the like. The concentration of the solvent may varies from 0.02 to 10 percent by weight. The mixing ratio of maleic anhydride high polymer and polyurethane is so determined that a ratio of allophanate bond to monomer unit of maleic anhydride ranges from 0.0001 to 0.01, taking into account molecular structures of maleic anhydride high polymer and polyurethane. In order to promote the insolubilization by evaporating the solvent from the coating on the body, the coating is thermally treated at a temperature ranging from 120 to 140° C., preferably, from 125 to 135° C. for 30 to 60 minutes, preferably, 30 to 50 minutes. During this thermal treatment, the coating is dried and then insolubilized.

Since the thus insolubilized coating in its original condition does not show the lubricity in the wet condition, the coating is then hydrophilized with a hydrophilizing agent to give hydrophilicity. This is done by immersing the coated body in a solution of the hydrophilizing agent for 3 to 120 minutes, or by exposing it to a vapor of the hydrophilizing agent for 3 to 120 minutes.

EXAMPLE 1

As an device body for guide wire, there is prepared a core wire of Ti-Ni alloy (Dymec) with a diameter of 0.48 mm coated with polyurethane ether (Pellethane 2363-80AE of The Dow chemical Co.). There is also prepared a mixed solution for a lubricating coating by dissolving methyl vinyl ether-maleic anhydride copolymer (GANTREZ AN-169 of GAF CHEMICALS, weight-average molecular weight: 67,000) and ether-polyester type polyurethane (Sanplane 1B-802 of SANYO CHEMICAL INDUSTRIES, Ltd., weight-average molecular weight: 50,000) in a weight ratio of 8:1 in methyl ethyl ketone adjusted to 1.125 wt % in concentration. The core wire is immersed in the mixed solution for 10 seconds, taken out therefrom and then heated at 130° C. for 30 minutes. The resin-coated wire is then immersed in a 40% methyl amine aqueous solution for 60 minutes, taken out therefrom and dried to prepare a medical guide wire. The resultant guide wire is subjected to surface lubricity test as mentioned below. Results are listed in Table 1.

Figure 1:
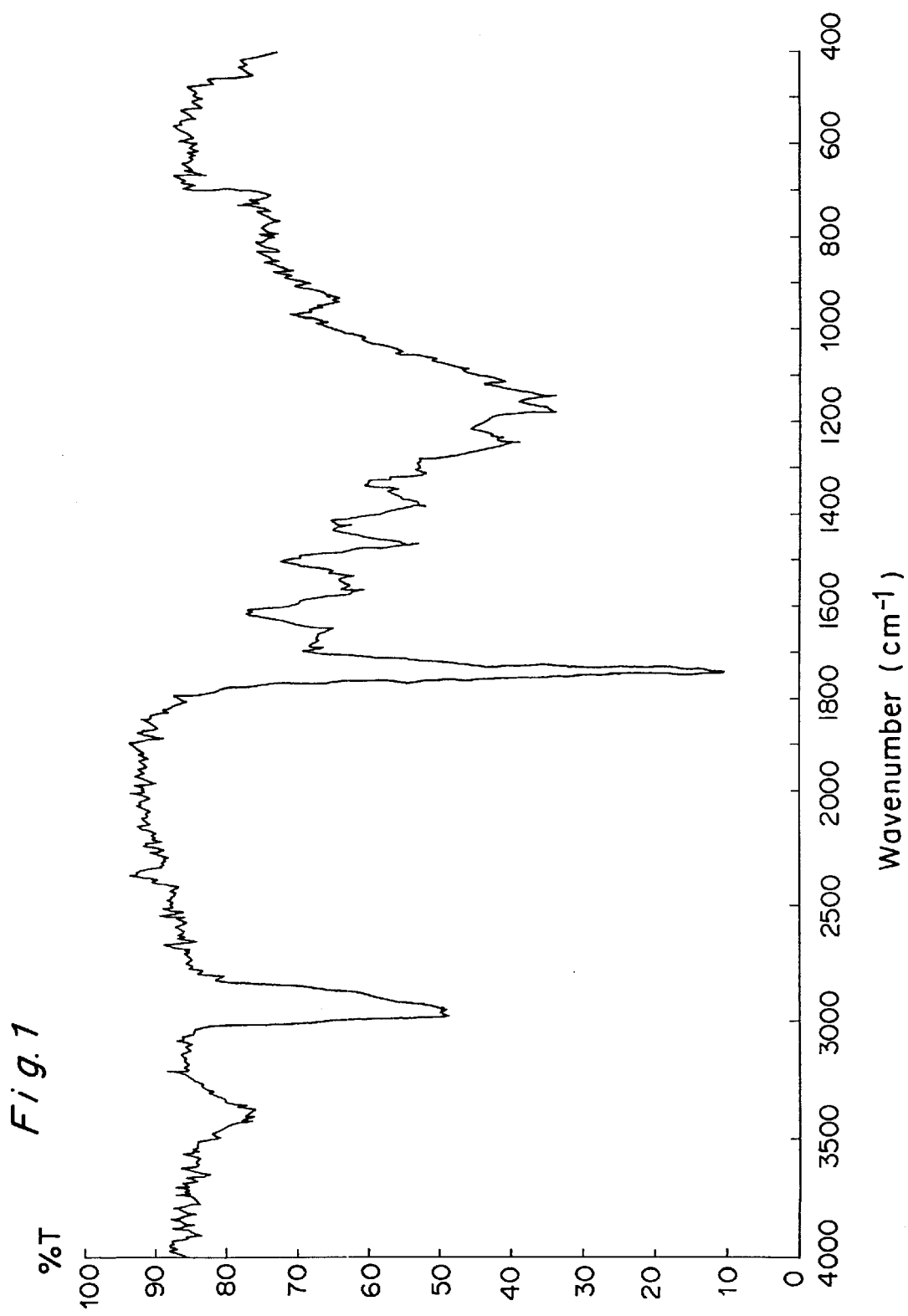
FIG. 1 is an infrared absorption spectrum of ether-ester type polyurethane before.
Figure 2:
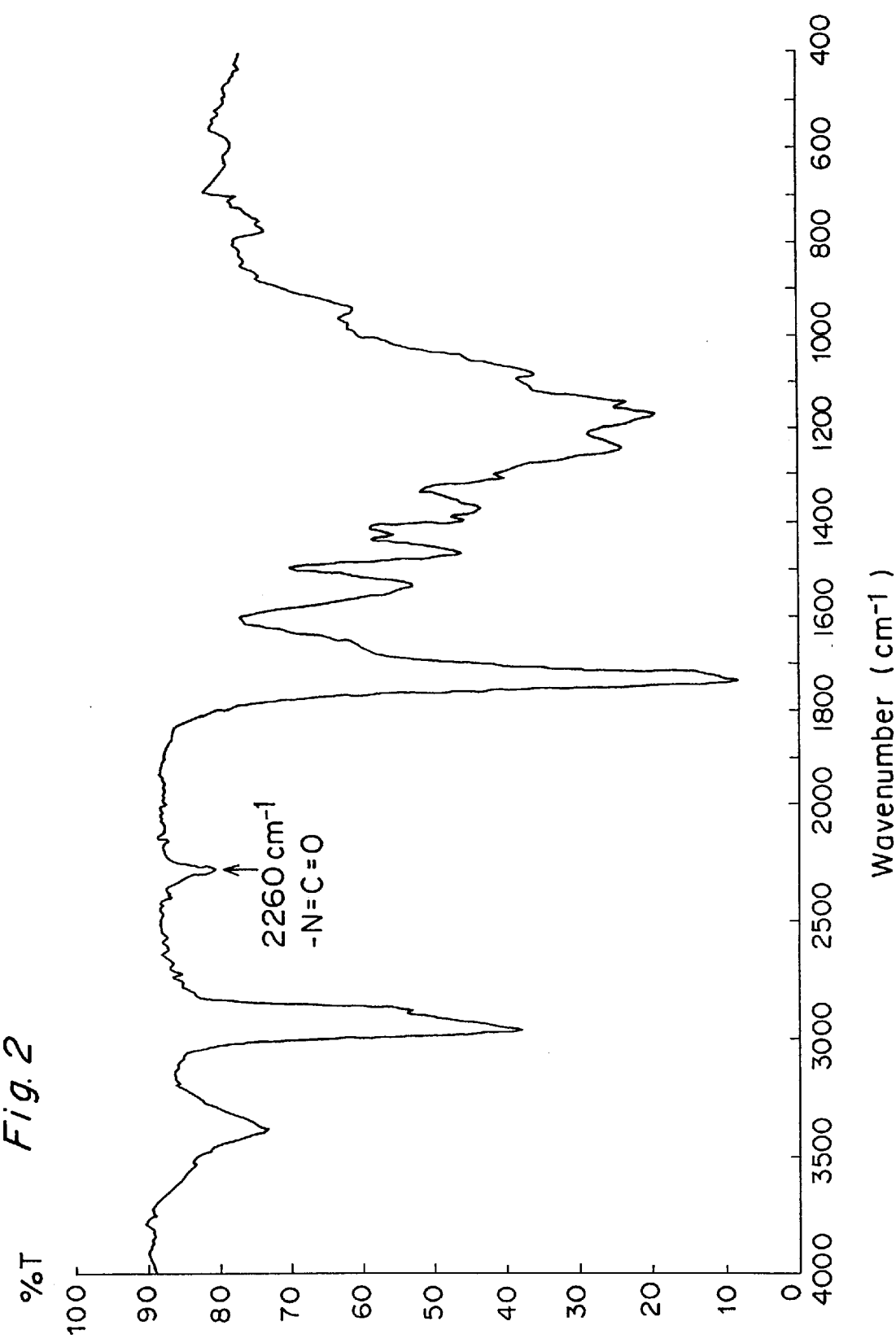
FIG. 2 is an infrared absorption spectrum of ether-ester type polyurethane after thermally treated.
Figure 3:
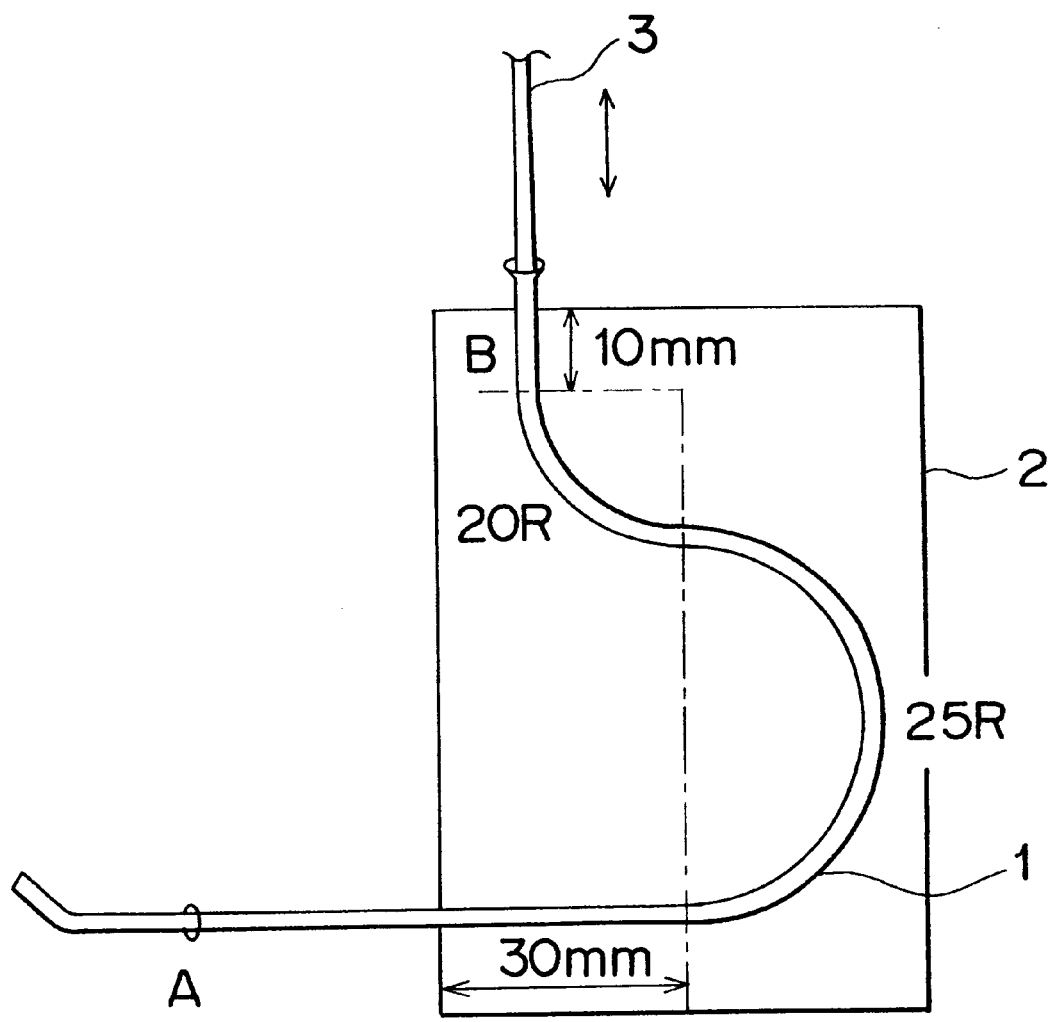
FIG. 3 is an explanatory view illustrating a procedure for performing a surface lubricity test.

FIG. 3 shows an explanatory view illustrating a procedure of a surface lubricity test of medical guide wires. The test is carried out as follows: Firstly, there is prepared an angiocatheter 1 having an inner diameter of 1.1 mm and being cut into a length of 25 cm. The angiocatheter 1 is bent into a shape shown in FIG. 3 and then fixed at a proximal end B thereof to a fixing plate 2. The guide wire 3, which has been previously wetted by immersing it in heparinized cow blood for 3 minutes, is inserted into a lumen of the angiocatheter 1 so that a distal end of the guide wire 3 is jutting out from a distal end A of the angiocatheter 1 as shown in FIG. 3. After this, the guide wire 3 is extracted from the angiocatheter 1. The insertion and extraction of the guide wire are repeatedly and a stress is measured every 10 times of repetition of the insertion and extraction of the guide wire with a tensile tester (Model S500D, SHIMADZU Corp.). A value of the frictional resistance between the guide wire and angiocatheter is determined as a half value of the sum of the stress obtained at the time of insertion and that obtained at the time of extraction.

EXAMPLE 2

Using the same coated core wire as that of Example 1, there is prepared a guide wire by immersing the core wire in a solution of a mixture of methyl vinyl ether-maleic anhydride copolymer and ether-ester type polyurethane dissolved in a weight ratio of 8:1 in methyl ethyl ketone adjusted to 1.125 wt % in concentration. After 10 seconds later, the core wire is taken out from the solution and heated at 130° C. for 30 minutes. The resultant resin-coated wire is immersed for 120 minutes in ethanol heated to 60° C., taken out therefrom, and then dried to prepare a medical guide wire. The resultant guide wire is subjected to the surface lubricity test in the same manner as in Example 1. Results are listed in Table 1.

COMPARATIVE EXAMPLE 1
(No polyurethane is used; reacted with amine)

Using the same coated core wire as that of Example 1, there is prepared a guide wire by immersing the core wire in a 1 wt % solution of methyl vinyl ether-maleic anhydride copolymer dissolved in methyl ethyl ketone. After 10 seconds later, the core wire is taken out from the solution and heated at 130° C. for 30 minutes. The resultant resin-coated wire is immersed in a 40 % methyl amine aqueous solution at room temperature for 60 minutes, taken out therefrom, and then dried to prepare a medical guide wire. The resultant guide wire is subjected to the surface lubricity test in the same manner as in Example 1. Results are listed in Table 1.

COMPARATIVE EXAMPLE 2
(No polyurethane is used; reacted with alcohol)

Using the same coated core wire as that of Example 1, there is prepared a guide wire by immersing the core wire in a 1 wt % solution of methyl vinyl ether-maleic anhydride copolymer dissolved in methyl ethyl ketone. After 10 seconds later, the core wire is taken out from the solution and heated at 130° C. for 30 minutes. The resultant resin-coated wire is immersed in ethanol heated to 60° C. After an elapse of 120 minutes, the resultant resin-coated wire is taken out from ethanol, and then dried to prepare a medical guide wire. The resultant guide wire is subjected to the surface lubricity test in the same manner as in Example 1. Results are listed in Table 1.

COMPARATIVE EXAMPLE 3
(No reaction with amine or alcohol)

Using the same coated core wire as that of Example 1, there is prepared a guide wire by immersing the core wire in a solution of a mixture of methyl vinyl ether-maleic anhydride copolymer and ether-ester type polyurethane dissolved in a weight ratio of 8:1 in methyl ethyl ketone adjusted to 1.125 wt % in concentration. After 10 seconds later, the core wire is taken out from the solution and heated at 130° C. for 30 minutes. The resultant guide wire is subjected to the surface lubricity test in the same manner as in Example 1. Results are listed in Table 1.

COMPARATIVE EXAMPLE 4
(Processed at a low temperature)

Using the same coated core wire as that of Example 1, there is prepared a guide wire by immersing the core wire in a solution of a mixture of methyl vinyl ether-maleic anhydride copolymer and ether-ester type polyurethane dissolved in a weight ratio of 8:1 in methyl ethyl ketone adjusted to 1.125 wt % in concentration. After 10 seconds later, the core wire is taken out from the solution, immersed in a 40 % methyl amine aqueous solution at room temperature for 60 minutes, taken out therefrom, and then dried to prepare a medical guide wire. The resultant guide wire is subjected to the surface lubricity test in the same manner as in Example 1. Results are listed in Table 1.

TABLE 1

| Number of sliding movement (Times) | FRICTIONAL RESISTANCE (g) | | | | | |
|---|---|---|---|---|---|---|
| | Ex. 1 | Ex. 2 | Comp. Ex. 1 | Comp. Ex. 2 | Comp. Ex. 3 | Comp. Ex. 4 |
| 0 | 4.5 | 4.0 | 4.0 | 6.5 | >50 | 7.0 |
| 10 | 4.5 | 4.0 | 6.5 | 6.5 | — | 34.0 |
| 20 | 4.5 | 4.5 | 7.0 | 7.0 | — | >50 |
| 30 | 4.5 | 4.5 | 10.0 | 8.0 | — | — |
| 40 | 5.0 | 4.5 | 15.0 | 11.0 | — | — |
| 50 | 6.0 | 6.0 | 20.0 | 15.0 | — | — |

As can be seen from the results shown in Table 1, the guide wires according to the present invention are excellent in surface lubricity and small in frictional resistance. In contrast therewith, the guide wires of comparative example 1 and 2 possess a low frictional resistance similar to that of the guide wires of the present invention at the beginning of their sliding movement, but the frictional resistance increases with the number of times of the sliding movement. Thus, the guide wires of comparative example 1 and 2 are poor in frictional durability. On the other hand, the guide wire of comparative example 3 employing no amine or alcohol possesses the same frictional resistance as that of the guide wires of examples 1 and 2 in pure water but does not possess the lubricity in the heparinized cow blood containing calcium ions. The guide wire of comparative example 4 thermally treated at a low temperature is poor in frictional durability since the frictional resistance thereof considerably increases from the beginning of the sliding movement.

Accordingly, the present invention makes it provide medical devices which show good surface lubricity when brought into contact with the blood and possesses high frictional durability, thus making it possible to lower pain of a patient to be treated.

We claim:

1. A method for producing medical devices comprising the steps of coating a solution of a mixture of maleic anhydride high polymer and polyurethane having allophanate bond on a surface of a body of a medical device, insolubilizing the resultant coating by heating, and then hydrophilizing it with a hydrophilizing agent.

2. The method for producing medical devices according to claim 1 wherein said hydrophilizing agent is a compound selected from the group consisting of ammonia, amines and alcohols.

* * * * *